(12) United States Patent
Hanselle et al.

(10) Patent No.: US 8,911,680 B2
(45) Date of Patent: Dec. 16, 2014

(54) DEVICE FOR COLLECTING AND TRIGGERED RELEASE OF A BIOLOGICAL SAMPLE

(75) Inventors: Thomas Hanselle, Hilden (DE); Markus Sprenger-Haussels, Hilden (DE); Christian Lenz, Hilden (DE); Daniel Groelz, Hilden (DE); Uwe Oelmueller, Hilden (DE)

(73) Assignee: Preanalytix GmbH, Hombrechtikon (CH)

( * ) Notice: Subject to any disclaimer, the term of this patent is extended or adjusted under 35 U.S.C. 154(b) by 711 days.

(21) Appl. No.: 12/521,390

(22) PCT Filed: Dec. 27, 2007

(86) PCT No.: PCT/EP2007/064563
§ 371 (c)(1),
(2), (4) Date: Sep. 3, 2009

(87) PCT Pub. No.: WO2008/080932
PCT Pub. Date: Jul. 10, 2008

(65) Prior Publication Data
US 2010/0317051 A1    Dec. 16, 2010

(30) Foreign Application Priority Data
Dec. 29, 2006    (EP) .................................. 06027074

(51) Int. Cl.
*G01N 33/48* (2006.01)
*B01L 3/00* (2006.01)
*A61B 10/00* (2006.01)
*C12N 15/10* (2006.01)
*G01N 1/40* (2006.01)
*G01N 1/02* (2006.01)
*G01N 35/00* (2006.01)

(52) U.S. Cl.
CPC ............ *B01L 3/5029* (2013.01); *C12N 15/1003* (2013.01); *A61B 10/0051* (2013.01); *A61B 2010/0074* (2013.01); *B01L 3/50825* (2013.01); *B01L 2300/042* (2013.01); *B01L 2300/046* (2013.01); *G01N 1/4022* (2013.01); *G01N 2001/028* (2013.01); *G01N 2035/00267* (2013.01); *Y10S 436/808* (2013.01)
USPC ........... 422/406; 422/430; 422/536; 422/561; 422/568; 436/63; 436/808

(58) Field of Classification Search
CPC .. C12Q 1/6806; C12Q 1/681; C12N 15/1003; C12N 15/1006
USPC ................. 422/405, 406, 430, 536, 561, 568; 436/63, 808
See application file for complete search history.

(56) References Cited

U.S. PATENT DOCUMENTS

| | | | |
|---|---|---|---|
| 4,144,760 A | 3/1979 | Schlueter et al. | |
| 4,317,454 A | 3/1982 | Bucalo | |

(Continued)

FOREIGN PATENT DOCUMENTS

| | | |
|---|---|---|
| EP | 0466009 | 1/1992 |
| JP | 11174048 | 7/1999 |

(Continued)

OTHER PUBLICATIONS

International Search Report for PCT/EP2007/064563 dated May 16, 2008 (3 pages).

(Continued)

*Primary Examiner* — Lyle Alexander
(74) *Attorney, Agent, or Firm* — Miles & Stockbridge, PC

(57) ABSTRACT

The invention relates to a system for collecting a biological sample comprising a container having at least one open end, a closure fitting on or in said at least one open end, a holding element connected to said closure and a solid matrix on which said biological sample is deposited, and optionally at least one processing agent, wherein said solid matrix is at least partially transferable into a liquid or dissolved state by changing at least one physico-chemical property of the environment of said matrix without disintegration of the biomolecules comprised in said biological sample deposited on said matrix.

23 Claims, 2 Drawing Sheets

(56) References Cited

U.S. PATENT DOCUMENTS

| | | | |
|---|---|---|---|
| 4,378,971 | A | 4/1983 | Schwartz |
| 4,393,141 | A | 7/1983 | Schlueter et al. |
| 5,096,062 | A * | 3/1992 | Burkardt et al. ............. 206/361 |
| 5,234,809 | A * | 8/1993 | Boom et al. ................. 435/91.2 |
| 5,266,266 | A * | 11/1993 | Nason .......................... 422/411 |
| 6,548,018 | B2 * | 4/2003 | DiCesare et al. .............. 422/52 |
| 6,627,226 | B2 | 9/2003 | Burgoyne et al. |
| 7,282,371 | B2 | 10/2007 | Helftenbein |
| 2004/0039188 | A1 * | 2/2004 | Gautsch et al. ............. 536/24.3 |
| 2004/0265169 | A1 * | 12/2004 | Haas et al. ...................... 422/56 |
| 2005/0276728 | A1 | 12/2005 | Muller-Cohn |
| 2006/0099567 | A1 | 5/2006 | Muller-Cohn |
| 2006/0115805 | A1 | 6/2006 | Hansen et al. |
| 2008/0199851 | A1 * | 8/2008 | Egan et al. ........................ 435/5 |

FOREIGN PATENT DOCUMENTS

| | | |
|---|---|---|
| WO | 82/01070 | 4/1982 |
| WO | 2004/038382 | 5/2004 |
| WO | 2004/053051 | 6/2004 |

OTHER PUBLICATIONS

Notice on the First Office Action Based on Chinese Application No. 200780048693.X; Date of Dispatch Oct. 14, 2010.

Notice of Rejection Based on Japanese Application No. 2009-543469; Date of Dispatch Mar. 21, 2012.

* cited by examiner

DEVICE FOR COLLECTING AND TRIGGERED RELEASE OF A BIOLOGICAL SAMPLE

CROSS REFERENCE TO RELATED APPLICATIONS

This application is a §371 National Stage Application of PCT/EP2007/064563 filed Dec. 27, 2007, which claims priority to European Application 06027074.1 filed Dec. 29, 2006.

BACKGROUND OF THE INVENTION

1. Field of the Invention

The invention relates to a system for collecting a biological sample, a method for collection of a biological sample, a kit, and a solid matrix for depositing a biological sample.

2. Description of Related Art

The analysis of biological material has long been of paramount importance in the diagnosis and treatment of disease, in food and environmental analysis and in forensic investigations, in particular using histological and pathological techniques. Recent technological advances have broadened the scope of such investigations by facilitating analysis of nucleic acids and proteins, which has opened up a large number of further possibilities. Gene activity can, for example, be determined directly by analysis of RNA, in particular the messenger RNA (mRNA) in cells. Quantitative analysis of transcription templates (mRNA templates) in cells by means of modern molecular biological methods, such as real time reverse transcriptase polymerase chain reaction (real time RT-PCR) or gene expression chip analysis enables, for example the identification of incorrectly expressed genes, so that, for example, metabolic disorders, infections or the presence of cancer can be detected. The analysis of DNA from cells by molecular biological methods, such as PCR (polymerase chain reaction), RFLP (restriction fragment length polymorphism), ALFP (amplified fragment length polymorphism) or sequencing permits, for example, the detection of genetic defects or the determination of the HLA (human leukocyte antigen) type as well as other genetic markers. The analysis of genomic DNA and RNA is also used as direct evidence for infectious agents, such as viruses, bacteria, and the like.

As the benefits of being able to analyse certain components of biological samples, for example nucleic acids or proteins, have become known, and as the analyses themselves have become more accurate and more accessible, such analyses have become important and frequently used tools available not only to the medical and veterinary professions, but also in a wide range of other areas, such as in the analysis of forensic materials, pharmaceutical products and intermediates, foods and environmental materials. In many of these areas it is important to maintain the integrity of the molecular structure of a sample.

Current procedures for the collection, handling and/or transport of biological samples such as blood, saliva or cells employ solid matrices such as cellulose- or cotton-based papers or swabs which differ significantly in their constituents and size.

For buccal or vaginal smears, swabs with a head made of cellulose, cotton or polymer fibres are frequently used. Swabs with heads made from cotton or synthetic fibre and swabs with ejectable paper heads, for example, are available from various commercial suppliers. After collection of the biological sample with such swabs, the swab is usually dried, stored and transported in a dried form, or stored and transported in a medium containing nutrients, antibiotics or other preservatives.

In order to recover the biological sample from the swab, it is generally necessary to wash the sample away from the swab support material. The washing away of the sample, which is often done by contacting the swab with a lysis reagent, is generally inefficient, incomplete and cumbersome. To maximise the amount of sample recovered, the support material of the swab head needs first to be separated from its shaft. Depending on the type of swab, this is accomplished by hand, by cutting with scissors, with a scalpel or a razor blade, or by bending or ejection. Separation processes involving cutting require the cutting device to be thoroughly cleaned and sterilised or disposed of after each use to avoid cross-contamination. Cross-contamination is a problem for all analytical methods, but particularly when working with samples destined for analysis of the nucleic acids, especially when employing an amplification process such as the polymerase chain reaction (PCR). Cross-contamination can, in the worst case, lead to distortion or even total falsification of the analysis results. The cutting process also represents a significant risk of injury to the operator, which can result in incorporation of foreign, potentially infectious material.

Ejectable swabs, where the head of the swab is separated from the shaft by bending or pressing the swab shaft, represent an expensive alternative.

Both types of swab have in common that the separated swab head carrying the biological material necessarily remains in the sample tube after separation from the swab shaft. The separated swab head then absorbs the transportation and/or storage solution, decreasing the accessible volume in the tube and hindering an efficient recovery of the sample with a minimal amount of liquid. Since often only very small amounts of sample are concerned, often, for example, on a nanogram scale, it is desirable to avoid as far as possible any loss or over-dilution of the sample.

Other biological samples such as blood are generally collected and stored using papers or cards, which can be treated or untreated. Treated papers are usually treated with several different agents which inactivate pathogens and prevent microbial growth and DNA degradation. In order to separate target biomolecules it is necessary to punch out smaller pieces of paper or card from the paper carrying the dried sample material. This process requires the cleaning and sterilisation of the punching device after each punching action in order to avoid cross-contamination. Disposable punching equipment is commercially available, but is cumbersome and expensive. In addition, the small weight of the paper punch together with static electricity and normal air movement make it difficult to handle the punch and to transfer it to the bottom of the sample preparation vessel.

Furthermore, for optimal yield of the target biomolecule it is necessary to cut the support material into small pieces before introducing it into the process to recover the biological sample. The cutting process is cumbersome and difficult to automate and represents another potential source of cross-contamination and risk of injury of the operator. Not cutting the support material results in reduced yields of recovered biological sample and compromised sensitivity in the downstream application, such as analysis of the sample.

After transfer of the solid matrix into the recovery reagent, which is usually a lysis reagent, the target biomolecules are usually eluted from the solid support. The elution of target biomolecules from the solid matrix is inefficient, cumbersome and tends to suffer from retention of a proportion of the biomolecules on the solid matrix. Elution can be carried out chemically, physically or enzymatically, or by a combination thereof. For further isolation of the target biomolecule it is necessary to separate the solid matrix from the liquid containing the biomolecule. This is done by removal of the liquid by pipetting, or by removal of the solid matrix. Both processes are inefficient and can lead to loss of sample material unless large quantities of solvent are used. They are also difficult to automate, because the solid matrix can interfere with a liquid handling system. It is also difficult to design an automated system that is able to remove blood spots or swabs reliably from a vessel. Another problem is the amount of liquid that remains trapped in the solid matrix. Since this liquid comprises the target biomolecules, its removal with the solid matrix causes decreased yield and sensitivity.

A number of different solid matrices in the form of a blood card or swabs, for example swabs with heads made from cellulose, cotton, Dacron® or other polymeric fibres is known and commercially available. There is also a choice of several recovery and purification methods. There is, however, a lack of a standard procedure and system for collection, storage, stabilisation and purification of biological samples. This makes it necessary to carry out a lot of optimisation work in order to optimise the yield and performance of a given combination of support material and sample preparation method.

WO 01/60517 describes a method for taking a blood sample using a receptacle for receiving a sample, preferably blood, containing a solution for stabilising nucleic acids and a solid phase capable of binding nucleic acids. The sample, once transferred to the vessel, subsequently needs to be removed from the solid phase by repeated washing. Furthermore, the collection of the sample requires the use of a cannula to transfer the liquid sample from its source into the receptacle, which has been placed under a low pressure. This prevents the use of the receptacle for small amounts of sample, for example blood from a finger prick or a heel prick from an infant, and for samples which cannot easily be transferred via cannula, or only with some discomfort for the sample donor, such as saliva, urine or cerebrospinal fluid. The receptacle is also not suitable for solid or semi-solid samples since a solid or semi-solid sample does not mix sufficiently with the stabilising solution in the presence of the solid phase.

EP 819 696 A2 describes a method of isolating nucleic acid from a biological sample and proposes the use of a nucleic acid-binding solid phase, preferably silica, which is mixed with the sample together with a chaotropic substance. The method requires a large number of washing, drying and elution steps in order to first isolate the solid phase with the thereto-bound nucleic acid from the solution and then isolate the nucleic acids from the solid phase. Furthermore, too large an amount of silica can be saturating, such that beyond a given amount of silica no further nucleic acid is obtained from the sample.

WO 02/072870 A2 describes a method and a device for storing genetic material. The head portion of the device is composed of a solid matrix for adsorbing genetic material and a preserving mechanism to protect the genetic material from degradation. The device can, however, only be used for liquid samples. Furthermore, the solid matrix must be cut into smaller portions in order to carry out analysis of the genetic material, resulting in loss of material and risk for the operator.

US 2006/0099567 and US 2005/0276728 propose a storage device for biological materials comprising dissolvable or dissociable matrix material which coats a sample well in a sample plate. The matrix material coating together with the sample is dried and subsequently rehydrated for sample recovery. The proposed system is particularly intended for use in high throughput systems. The biological sample is, however, first collected using conventional techniques and as such the proposed system does not address the above-mentioned problems associated with collection of the sample and recovery of the sample from the collecting device. In addition, these documents are silent about the benefits of providing a sample system with means for dissolving the matrix material in the presence of a chaotropic salt.

SUMMARY OF THE INVENTION

It is an object of the present invention to overcome the disadvantages known from the prior art.

Another object of the present invention is to enable a simpler and faster collection and recovery of a biological sample from a device used to collect the sample, compared to sample recoveries known from the prior art.

It is also an object of the present invention to reduce the loss of biological material when recovering a biological sample from a device used to collect the sample, without needing to use large quantities of solvent.

It is a further object of the present invention to avoid the use of cutting and/or punching devices in the recovery of a biological sample from a collecting device.

Another object of the invention is to provide a system for collecting and handling a biological sample which can be applied to a range of different types of biological sample.

A further object of the invention is to provide a system of collecting and handling a biological sample which is compatible with automated processes.

It is a further object of the present invention to provide an integrated sampling or collecting and storage device and a method for using or further processing such integrated device.

It is a further object of the present invention to provide a method for dissolving or liquefying a sampling device without substantial degeneration of the biomolecules contained in said biological sample.

It is a further object of the present invention to provide a method for dissolving or liquefying a sampling device wherein the interaction of water molecules with biomolecules contained in said biological sample is modified without substantial degeneration of the biomolecules contained in said biological sample.

A contribution to solving the problems arising from present techniques and to at least partly overcoming their disadvantages is made according to the present invention by a system for collecting a biological sample comprising a container having at least one open end, a closure fitting on or in said at least one open end, a holding element connected to said closure and a solid matrix on which said biological sample is deposited, wherein the material of said solid matrix is at least partially transferable into a liquid or dissolved substantially without disintegration of biomolecules contained in said biological sample by changing at least one physico-chemical property of the environment of said matrix, in the presence of at least one chaotropic substance and optionally at least one solution of a high ionic strength. Preferably, the solid matrix is capable of being used for direct collection of said biological sample.

DETAILED DESCRIPTION OF A PREFERRED EMBODIMENT

Detailed Description of the Invention

Figure 1:
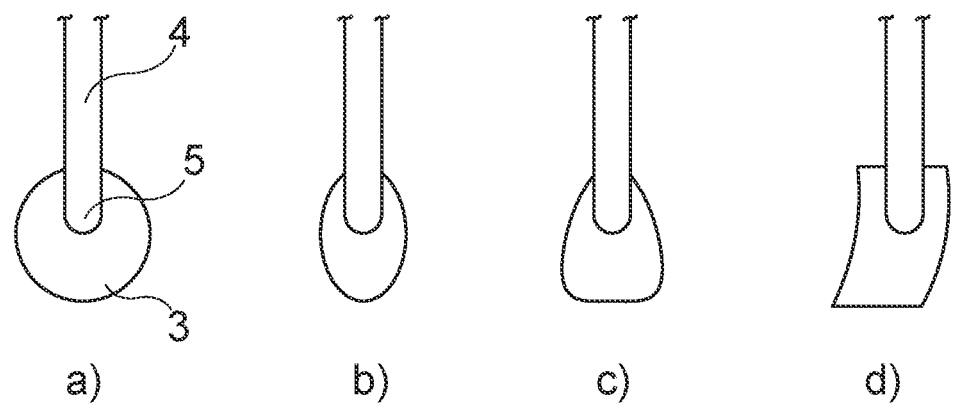
FIGS. 1-3 depict embodiments of the present invention.
Figure 1:
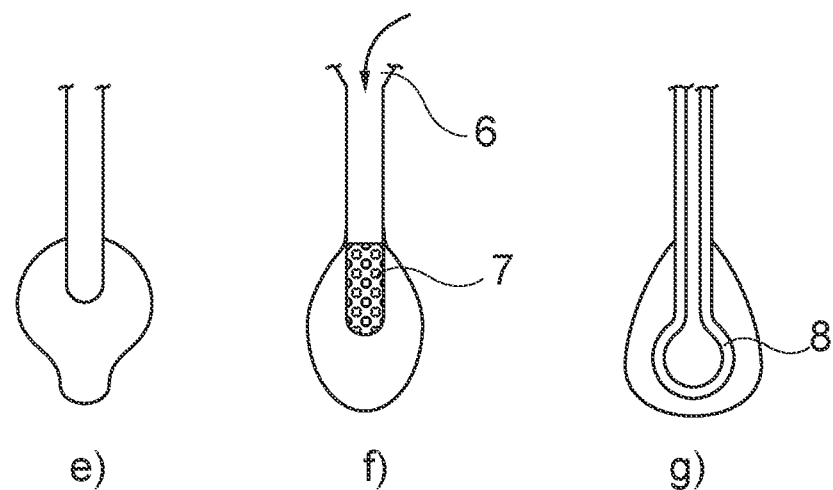

The biological sample can be a sample collected from any biological source and is preferably a biological sample of any human, animal and plant material. As biological samples according to the invention are generally considered, without limitation, cell-free and cell-comprising sample material, plasma, bodily fluids, such as blood, sputum, saliva, urine, cerebrospinal fluid, sperm, serum as well as cells, leukocyte fractions, crusta phlogistica (buffy coat), faeces, swabs, aspirates, tissue samples of any sort, tissue fragments and organs, vaccines, food or environmental samples which comprise free or bound nucleic acids or nucleic acid-carrying cells, plants, plant extracts and plant parts, bacteria, viruses, yeasts and other fungi, or extracts therefrom, other eukaryotes and prokaryotes, among others, in particular all possible tissue samples, tissue fragments, organs, whole organisms and individual cells. Preferred biological samples comprise a biological material such as any bodily fluid, such as blood, saliva, urine, semen, sputum or cerebrospinal fluid, an epithelial cell, a smear, a bacterium, a virus, a vaccine, a fine needle aspirate, a biopsy, a forensic sample, an isolated cell, a fungus or a part or an extract of a fungus, a plant or a part or an extract of a plant.

Direct collection is understood to describe the fact that said matrix has been used directly during the collection of the biological sample. A non-limiting example of such use would be a so called swab that would be brought in close contact with said biological sample, e.g. by rubbing at the mucous membrane in the interior of the mouth or the like. Non-direct collection in contrast would be if another collection device was used for collecting the biological sample and the biological sample would have been then deposed by that collection device on the matrix according to the invention, e.g. by washing it from said collection device on said matrix. This also impacts the choice of matrix material which must fit the special purpose. Obviously, selection criteria will be biocompability (e.g. non-toxic, stable to the body fluid, stable under the sampling conditions), fitness to be sterilized, long term stability Biomolecules are organic molecules present in a biological fluid such as nucleic acids, proteins, enzymes, and the like as the typical skilled in the art will immediately appreciate.

In a preferred embodiment the biological sample comprises a protein and/or nucleic acid or nucleic acids. The term "nucleic acid" is here used in its broadest sense and comprises ribonucleic acids (RNA) and deoxyribonucleic acids (DNA) from all possible sources, in all lengths and configurations, such as double stranded, single stranded, circular, linear or branched. All sub-units and sub-types are also comprised, such as monomeric nucleotides, oligomers, plasmids, viral and bacterial nucleic acids, as well as genomic and non-genomic DNA and RNA from animal and plant cells or other eukaryotes or prokaryotes, messenger RNA (mRNA) in processed and unprocessed form, transfer RNA (tRNA), heterogeneous nuclear RNA (hn-RNA), ribosomal RNA (rRNA), complementary DNA (cDNA)), genomic DNA (gDNA), siRNA, miRNA, as well as all other conceivable nucleic acids.

Modification of the interaction of water molecules with biomolecules contained in said biological sample is being understood as decreasing or totally destroying any interaction of water with biomolecules, preferably nucleic acid, such as formation of a hydrate shell or any other hydrogen bond structures between the biomolecules contained in said biological sample and water molecules. Surprisingly, it has been found that said modification of the interaction of water molecules with biomolecules does result in higher yield and or better performance of the method according to the invention. Preferably, said modification of the interaction of water molecules with biomolecules is performed by a chemical means provided together with the system according to the invention, such as a tube (e.g. a Vacutainer®) being coated on the inside or prefilled with solid granules or the like with/of chemical substances such as chaotropic substances or salts (jointly or individually referred to as chaotrope) or the like. It is also preferred that the chemical substances are provided in liquid or gel form, e.g. a prefilled tube (e.g. a Vacutainer®)

Substantially without disintegration according to the invention is preferably understood to mean that the biomolecule remains substantially intact and does not disintegrate into its component parts when the solid matrix is at least partially transferred from the solid state into a dissolved or liquid state. It can, however, also mean that at least one component of the biological sample remains substantially intact and does not disintegrate into its respective component parts when the solid matrix is at least partially transferred from the solid state into a dissolved or liquid state.

The container having at least one open end can have any form which is suitable for collecting and optionally treating and/or processing preferably while allowing a modification of the interaction of water molecules with biomolecules contained in said biological sample. The container can, for example, be in the form of a vial, a tube, a cup, a bowl, a flask, a jar or a bottle. The container can be disposable, i.e. capable of being used only once, or it can be reusable, preferably after appropriate cleaning and/or sterilization. The container is preferably made at least partially from a material such as plastic or glass which is preferably at least partially inert to the substances and materials comprised in the system according to the invention and in particular to the reagents or compositions with which it might come into contact. The container material is, for example, preferably at least partially inert to additives or substances which might be used for processing, isolation and/or treatment of biomolecules, especially nucleic acids, such as formation of a hydrate shell or any other hydrogen bond structures between the biomolecules contained in said biological sample and to the sample itself and/or components thereof, and can preferably be heated, for example to temperatures at which the solid matrix of the device according to the invention melts, or to sterilization temperatures. The container material is preferably also non-breakable in routine use, including during possible heating, cooling, freezing, sterilisation, transport, storage or other processes where it is handled by a person or by a device, for example in an automated or semi-automated device, in particular in a high throughput device. It is also possible that the vessel is made of a material which allows the vessel to be reused if so desired, preferably after appropriate washing and/or sterilisation.

It is also conceivable that the vessel material comprises agents which assist in the conservation of a biological sample stabilised therein, such as antimicrobials, fungicides or inhibitors which inhibit degradation of the sample to be stabilised or of components thereof, such as an RNase inhibitor, these agents being capable of being released upon contact with the liquid or with the biological sample or with both.

The container is provided with a closure fitting on or in the at least one open end, for at least partially closing the container. Examples of possible closures are known to the person skilled in the art and can be, for example, caps, screw closures, stoppers and the like. The closure can be either disposable or reusable.

A holding element is connected to the closure, preferably such that the holding element extends into the container when the closure is fitted on or in the at least one open end of the container. It is preferred that the at least one solid matrix of the invention, or the solid matrix and the holding element according to the invention, is removable from the closure. It is also possible that the holding element according to the invention is permanently attached to the closure and a fresh solid matrix is applied anew to the holding element for each new use. The holding element according to the invention can be flexible or rigid and is preferably rigid. Rigid according to the invention is understood as meaning that a certain degree of flexibility can also be present, such that it may be possible to flex or bend the holding element to a small extent by application of slight force, for example by a person using the device, but the holding element recovers and retains substantially its original form when a force is no longer applied.

It is preferred according to the invention that the holding element is in the form of a shaft with a tip, a cup, paper cards or sheets, preferably in the form of a shaft with a tip. The holder according to the invention is preferably not in the form of a sample plate comprising one or a plurality of sample wells.

If the holding element is in the form of a shaft with a tip, the solid matrix can be attached to the holding element by any element or in any way which is considered suitable by the skilled person. It is preferred according to the invention that the holding element is attached in non-mechanically detachable fashion by means of the tip to the solid matrix. The term "non-mechanically detachable" means that the holding element can be detached from the solid matrix by non-mechanical element, for example by changing a physico-chemical property. Mechanical elements such as, for example, pulling, twisting, cutting, punching or bending are, however, not excluded as alternative or secondary means of at least partially detaching the holding element from the solid matrix.

It is conceivable that the holding element comprises a device for local heating or cooling of the solid matrix, for example an opening which extends through the holding element to the region of the solid matrix, without contacting the solid matrix, and which carries, for example, an electrical current or a heating substance capable of effecting heating, or a cooling substance, such as a cold fluid, for example a cold liquid and/or a cryogen. It is also possible that the holding element comprises an opening which extends through the holding element to the region of the solid matrix and which is also open to the solid matrix. Such an opening could be used to add a liquid, for example to pass a liquid through the solid matrix, in order to wash it, cool it, or to cause it to at least partially be transferred into a liquid or dissolved state, to at least partially release the biological sample or at least one component thereof.

The holding element can be in any material which is suitable for its purpose, preferably a material which does not react with reagents which effect or assist the transfer of the solid matrix from the solid state into a liquid state. It is also preferred that the material or materials of the holding element do not absorb the liquid or dissolved state comprising the biological sample. Preferred materials for the holding element are plastics such as polypropylene, polyethylene or polyurethane, metals, wood, card or card which has been treated, for example to prevent it from absorbing the solid matrix material liquid or dissolved state comprising the biological sample.

The solid matrix on which the biological sample is deposited can have any form or shape which is suitable for the collection of a biological sample. In a preferred embodiment of the device according to the invention, the solid matrix is in the form of a round or elongated ball, a bulb, a mesh, a stick, a woven bulb, a paper, a card, a particle, a bead, a rod, a plug or a filter.

The unit comprising holding element and solid matrix according to the invention can be in any form which is considered suitable by the skilled person. It is particularly preferred according to the invention that the solid matrix is held by the holding element and that the unit comprising holding element and solid matrix according to the invention has a rod-like form. Rod-like according to the invention is understood as meaning an elongated form which can be, for example, an elongated substantially cylindrical form, whereby the diameter of the rod need not be uniform along the entire length. The rod-like unit comprising holding element and solid matrix preferably comprises a shorter first part and a second part which is longer than the first part, the average diameter of the first part preferably being greater than the average diameter of the second part. The diameter of the second part is preferably within the range from 0.1 mm (millimeter) to 10 mm, more preferably within the range from 0.5 mm to 8 mm, more preferably within the range from 1 mm to 5 mm, yet more preferably within the range from 1.5 mm to 4 mm, most preferably within the range from 2 mm to 4 mm. The average diameter of the first part is preferably greater than the diameter of the second part by a factor within the range from 1.5 to 20, preferably within the range from 2 to 15, more preferably within the range from 2 to 12, yet more preferably within the range from 2 to 10. In a preferred aspect of the invention the second part of the unit is the holding element and the first part of the unit is the solid matrix.

In a preferred embodiment the unit comprising holding element and solid matrix according to the invention is in the form of a swab, a paper or a card. The swab can be, for example, a buccal, nasal, pharyngeal, eye, cervical, anal, cloacal or other swab.

In the system according to the invention, the material of the solid matrix on which the biological sample is deposited is at least partially transferable from the solid state into a dissolved or liquid state for at least partially releasing the collected biological sample when at least one physico-chemical property of the environment of the matrix is changed, substantially without disintegration of the biomolecules deposited on the matrix, preferably in the presence of at least one chaotrope. The term "solid state" is understood to mean a physical state of the solid matrix. The dissolved or liquid state of the solid matrix according to the present invention, on the other hand, can be in the form of a solution, dispersion, suspension, emulsion or melt. The term "at least partially transferable" according to the invention should be understood as meaning that at least part of, preferably most of and most preferably all of the solid matrix comprised in the method according to the invention can be transferred from the solid state into a dissolved or liquid state. It is preferred according to the invention that changing at least one physico-chemical property triggers at least a partial, preferably to at least 10 wt. %, more preferably to an amount of at least 50 wt. %, even more preferably to an amount of at least 75 wt. % and most preferably a full transfer into said liquid or dissolved state. The transformation from the solid state into a dissolved or liquid state is preferably in the form of a dispersing, an emulsifying, a suspending, a dissolving or a melting, preferably a dispersing, a dissolving or a melting, and preferably occurs by changing at least one physico-chemical property according to the invention.

Substantially without disintegration according to the invention is preferably understood to mean that all the biomolecules comprised in the biological sample remain substantially intact and do not disintegrate into their component parts when the solid matrix is at least partially transferred from the solid state into a dissolved or liquid state. It can, however, also mean that at least one component of the biological sample remains substantially intact and does not disintegrate into its respective component parts when the solid matrix is at least partially transferred from the solid state into a dissolved or liquid state.

Physico-chemical properties which can be changed to result in an at least partial transfer of the solid state of the matrix to a dissolved or liquid state comprise, for example, contacting the solid matrix with a liquid in which it at least partially dissolves, or contacting the solid matrix with a reagent or with a composition which comprises at least one component which enhances or causes its transfer into a liquid or dissolved state, or subjecting the solid matrix to a temperature or pressure at which it melts. These physico-chemical properties can have an effect alone or in combination with each other or with other physico-chemical properties which, when changed, effect, catalyse or otherwise in any way enhance a transfer of the solid matrix into a liquid or dissolved state.

It is preferred according to the present invention that the solid matrix should be at least partially solid, preferably substantially solid, more preferably entirely solid, under the collection conditions employed for collecting the biological sample. This is particularly preferable if the sample is to be collected directly at its source. The collection conditions can be physiological conditions when collecting a sample from a living organism, for example a sample from a human, animal or plant. Physiological conditions are generally characterized as the typical conditions of physico-chemical properties such as temperature, pH, concentration of electrolytes, presence of enzymes or other components, among others, which are present in the organism, in particular in the part of the organism which is to be collected as a sample, in its natural state. Thus for a healthy human, for example, physiological temperatures fluctuate but generally range from 36° C. to 38° C. These temperatures can be altered by several degrees in an ill human, for example reaching as high as 44° C. or as low as 30° C. Physiological pH in a human is generally considered to be 7.4, the pH can, however, vary depending on the location in the body, whereby pH in the stomach, for example, generally lies in the range of from 1.5 to 3.

The solid matrix in both the solid state and in a liquid state is preferably stable to storage at ambient conditions of temperature and humidity, in order to avoid as far as possible the necessity for special packaging to protect the system, and for an extended life of the system. If the system should be sterile, any necessary packaging may be used which preferably maintains the sterility of the system, in particular the sterility of the solid matrix.

It is particularly preferred according to the invention that the biological sample is applied to the solid matrix by means of directly contacting the solid matrix with the biological sample and preferably by collecting the biological sample directly from its source using the solid matrix (see direct collection). The biological sample is preferably not poured onto the solid matrix according to the invention.

The transfer of the at least one solid matrix from the solid state into a dissolved or liquid state, preferably in the presence of at least one chaotrope, preferably occurs in the course of at least one of stabilization, transport, or storage of the solid matrix carrying the biological sample, or in the course of processing the biological sample, for example by purification of target biomolecules from the solid matrix. It is advantageous that the biological sample does not dry on the solid matrix. Thus, for example, a stabilizing material, preferably in the form of a stabilizing liquid which is applied to stabilize the biological sample can itself effect or enhance an at least partial dissolving of the solid matrix to at least partially release the sample or a component thereof, or can comprise an agent which effects or enhances a dissolving of the solid matrix to at least partially release the sample or a component thereof. This at least partial dissolving of the solid matrix can then occur while the solid matrix comprising the biological sample is in contact with the stabilizing material, preferably the stabilizing liquid, during stabilization, transport, handling or storage of the sample.

Another possibility is that an agent which causes or enhances the dissolving of the solid matrix is applied, preferably but not necessarily in the form of a liquid, in the course of processing the biological sample, for example in the course of isolation and/or preparation of the biological sample or a component thereof for analysis, or isolation and/or purification of target biomolecules. It is also possible that the temperature is increased or decreased, preferably increased, during at least one of stabilization, transport, processing and storage of the solid matrix which is in contact with the biological sample. This would cause a meltable solid matrix to be at least partially transferred from the solid state to a liquid state and preferably to at least partially release the biological sample or a component thereof substantially without disintegration of the biological sample according to the invention.

In one preferred embodiment of the system according to the invention, the material of the solid matrix is at least partially soluble in at least one solvent. According to this embodiment, the solid matrix is preferably at least partially soluble, preferably fully soluble, for at least partially releasing the collected biological sample. In this embodiment, the change of physico-chemical property of the environment of the matrix consists of addition of a solvent.

In one aspect of the invention the solid matrix can be at least partially dissolved by at least one organic solvent as reagent. In this case the solid matrix is preferably a polymer which can be at least partially dissolved by at least one organic solvent, preferably a polymer selected from polymers comprising at least one carboxylic acid-comprising monomer, polymers comprising at least one carboxylic acid group-comprising monomer and at least one ethylenically unsaturated monomer, polymers comprising at least one monomer comprising at least one acid group and at least one ethylenically unsaturated group, polymers comprising at least one monomer comprising at least one ring system, preferably at least one ring comprising at least one hetero-atom, preferably at least one oxygen-comprising ring, polymers comprising at least one ester group. Examples of preferred polymers are acidic polymethacrylates, which are soluble in iso-propanol, cellulose acetate phthalate, which is soluble in acetone, crotonic acid copolymers, such as vinyl acetate, which are well soluble in dichloromethane and very well soluble in acetone, polyvinylacetate phthalate, which is well soluble in 90% ethanol, or hydroxypropylmethlcellulose-acetate succinate, which is well soluble in acetone.

In one aspect of the system according to the invention, the material of the solid matrix is at least partially meltable by increasing the temperature, preferably in the presence of at least one chaotrope.

It is advantageous if the solid matrix is solid at the temperature of collection of the biological sample. If a sample is to be collected from a living person or animal, it is preferred that the solid matrix is solid at physiological temperatures, and that the solid matrix gets transferred to the liquid state above physiological temperatures, preferably at temperatures above 45° C., preferably at temperatures within the range from 45° C. to 95° C., preferably at temperatures within the range from 45° C. to 85° C., more preferably at temperatures within the range from 45° C. to 75° C., even more preferably at temperatures within the range from 45° C. to 70° C., most preferably at temperatures within the range from 45° C. to 65° C. It is preferred that the biological sample can be released without being damaged or degraded. The solid matrix is thus preferably meltable at a temperature at which the biological sample and its components are not destroyed or degraded. If a sample is to be collected from a dead person or animal, or from a plant, fungus, food, or from the environment, the solid matrix can melt at a lower temperature, provided that it is solid at the temperature of collection of the sample. The solid matrix preferably has a sharp melting point, i.e. it melts over a small temperature range, preferably over a temperature range of less than 5° C., more preferably over a temperature range of less than 4° C., even more preferably over a temperature range of less than 3° C., most preferably over a temperature range of less than 2° C.

Materials which are suitable as meltable solid matrices according to the invention are, for example, fats which are solid at physiological temperatures, such as cocoa butter or palm fat. A further preferred meltable solid matrix according to the invention is a wax with a melting point above 45° C. and a plastic structure at normal ambient temperatures. Suitable waxes can be animal and/or insect waxes, for example beeswax. Chinese wax produced by scale insects coccus ceriferus, shellac wax from the lac insect coccus lacca, spermaceti from the head cavities and blubber of the sperm whale and lanolin (wool wax) from the sebaceous glands of sheep are mentioned as examples. Examples of suitable vegetable waxes are bayberry wax from the suface of the berries of the bayberry shrub, candelissa wax from the Mexican shrubs *Euphorbia cerifera* and *E. antisyphilitica*, carnauba wax from the leaves of the Carnauba Palm, Castor carnauba palm, castor wax, catalytically hydrogenated castor oil, esparto wax, a byproduct of making paper from esparto grass, Japan wax, a vegetable tallow (not a true wax) from the berries of *Rhus* and *Toxicodendron* species, jojoba oil pressed from the seeds of the jojoba bush, a replacement for spermaceti, ouricury wax from the Brazilian feather palm and rice bran wax obtained from rice bran. Mineral waxes are also suitable as meltable solid matrix according to the invention, such as ceresin waxes, montan wax extracted from lignite and brown coal, ozocerite found in lignite beds and peat waxes. Another group of materials suitable as solid matrix according to the invention is high molecular weight alkane hydrocarbons such as paraffin, an odourless, tasteless petroleum wax with a typical melting point between 47° C. and 65° C. Also suitable are synthetic waxes such as polyethylene waxes based on polyethylene, Fischer-Tropsch waxes, or chemically modified waxes—usually esterified or saponified, substituted amide waxes and polymerised α-olefins. Further possible solid matrices are monoterpenes such as thymol, found in oil of thyme and extracted as a white crystalline substance of a pleasant aromatic odour and strong antiseptic properties, with a melting point of 48-52° C., or camphene, a bicyclic monoterpene with a melting point of 51-52° C. Another group of meltable solid matrix comprises sugar, i.e. sucrose in combination with an aqueous lysis buffer. A further possible solid matrix is low melting agarose with a melting point below 65° C.

In another embodiment of the system according to the present invention, the material of the solid matrix is at least partially transferable into a liquid or dissolved state by addition of at least one reagent, preferably soluble, preferably fully soluble, for at least partially releasing the collected biological sample, preferably in the presence of at least one chaotrope. In this embodiment, the change of physico-chemical property of the environment of the matrix preferably can consist of addition of a solvent and optionally at least one compound selected from reagent(s), enzyme(s), acid(s), and base(s). It is also possible that the change of physico-chemical property of the environment consists of addition of at least one compound selected from reagent and optionally a solvent.

The reagent can comprise at least one chelator or salt thereof, (s), enzyme(s), acid(s) and base(s) and optionally in the presence of one or more liquids.

The solid matrix can thus preferably be dissolved, for example, by at least one of contacting it with a liquid in which it dissolves and contacting it with a reagent or with a composition which effects, catalyses or otherwise enhances its dissolution, preferably in the presence of at least one chaotrope. It is also conceivable that, for example, the solid matrix can be contacted with a liquid in which it does not dissolve and then is at least partially dissolved by further contacting with a reagent or composition. It is also possible that the solid matrix is first contacted with a reagent or composition and then contacted with a liquid. The reagent or composition can be in solid or liquid form. The term "liquid form" is understood to mean at least one solvent, or at least one solution in any conceivable solvent or mixture of solvents which is considered suitable by the person skilled in the art, or reagents or compositions which are liquid at the desired operating temperature, as well as melts.

In one aspect of the invention the solid matrix can be at least partially dissolved by at least one organic solvent as reagent, preferably in the presence of at least one chaotrope. In this case the solid matrix is preferably a polymer, preferably a polymer selected from polymers comprising at least one carboxylic acid-comprising monomer, polymers comprising at least one carboxylic acid group-comprising monomer and at least one ethylenically unsaturated monomer, polymers comprising at least one monomer comprising at least one acid group and at least one ethylenically unsaturated group, polymers comprising at least one monomer comprising at least one ring system, preferably at least one ring comprising at least one hetero-atom, preferably at least one oxygen-comprising ring, polymers comprising at least one ester group. Examples of preferred polymers are acidic polymethacrylates, which are soluble in iso-propanol, cellulose acetate phthalate, which is soluble in acetone, crotonic acid copolymers, such as vinyl acetate, which are well soluble in dichloromethane and very well soluble in acetone, polyvinylacetate phthalate, which is well soluble in 90% ethanol, or hydroxypropylmethlcellulose-acetate succinate, which is well soluble in acetone.

The reagent according to the invention can comprise at least one chelator or salt thereof. The solid matrix can thus be at least partially transferred into a liquid or dissolved state with assistance from at least one chelator or salt thereof as reagent, in the presence of a solvent or optionally one or more liquids as defined above. A suitable chelator according to the invention comprises at least 2, 3, 4, 5, 6, 7 or 8 coordinating sites, preferably 2 to 6, more preferably 4 to 6 binding sites.

The reagent can comprise at least one ionic strength and/or chaotropic stabiliser, preferably at least one chaotropic salt, preferably in the form of a solution in an organic or inorganic solvent, whereby preferred organic solvents are those mentioned above as solvent, and preferred as inorganic solvent is water. Further it is preferred that the solid matrix is at least partially transferred into a liquid or dissolved state in the presence of at least one chaotropic substance (chaotrope), optionally in the presence of at least one solution of a high ionic strength, as reagent. The ionic strength, I, of a solution is a function of the concentration of all ions present in a solution. On a molality basis, $$I_m = \frac{1}{2} \sum m_B z_B^2$$

where the sum goes over all the ions B. $z_B$ is the charge number of ion B. (see e.g. IUPAC Compendium of Chemical Terminology, Electronic version, http://goldbooklupac.org/I03180.html).

Solutions of high ionic strength are known to the skilled in the art and do have an ionic strength in the range of 0.1 to 50, preferably 5-30, especially preferred 7-24. Chaotropic substances are known from U.S. Pat. No. 5,234,809 and other related patents which for the purposes of the US—patent practice are herewith incorporated by reference. A chaotrope is an agent which causes molecular structure to be disrupted, in particular molecular structures formed by non-covalent forces such as hydrogen bonding, salt bridges, and the hydrophobic effect. As chaotrope, guanidinium salts are preferred, whereby guanidinium isothiocyanate or guanidinium hydrochloride are particularly preferred. The at least one chaotrope is preferably present in solution, preferably in aqueous solution, at a concentration within the range from 0.01-15 (mol/l), preferably 1 to 6 M (mol/l), more preferably within the range from 2 to 5.9 M, even more preferably within the range from 3 to 5.8 M and most preferably within the range from 4 to 5.7 M. In this aspect of the method according to the invention, therefore, the solid matrix can be at least partially transferred into a liquid or dissolved state by being contacted with a substance or a composition that effects, catalyses or otherwise enhances the disruption of the water structure.

It is also conceivable according to a further aspect of the present invention that the solid matrix is at least partially transferable into a liquid or dissolved state by contacting with at least one enzyme, preferably in the presence of at least one chaotrope. The solid matrix can thus comprise at least one material which can be at least partially transferred from the solid state into a dissolved or liquid state in the presence of at least one enzyme.

The enzyme is preferably at least one enzyme selected from the group consisting of proteases, cellulases, amylases, glycanases, chitinases, lysozymes, lipases, esterases, pectinases, pectolyases, agarases which can be present alone or in combination with at least one other enzymes, reagent, acid or base.

It is preferred according to the invention that the solid matrix comprises at least one of a peptide, an ester, a polysaccharide and cellulose and/or a derivative of at least one thereof. These preferred materials are particularly advantageous if the solid matrix is to be transferred into a dissolved or liquid state in the presence of at least one enzyme. They are also preferably capable of dissolving or being at least partially transferred into a liquid or dissolved state when at least one other physico-chemical property is changed. Examples of preferred solid matrices are materials linked by peptide bonds that are degradable by proteases, materials linked with ester bonds that are degradable by esterases and/or by changing pH; polysaccharides linked by glycosidic bonds that are degradable by polysaccharide-degrading enzymes such as amylases, chitinases, cellulases, or by other enzymes or reagents.

A preferred solid matrix according to the invention comprises or has a surface comprising a cotton-based material. By "cotton" according to the invention is preferably understood a natural polymer of cellulose, preferably a polysaccharide composed of 100-10,000-D-glucose molecules connected via one to four glycosidic bonds. Cellulose according to the invention is insoluble in aqueous solutions but can be solubilised by degrading the polymer to -D-glucose. This degradation is preferably mediated by the enzyme cellulase, for example as commercially available from Novozyme, or Sigma.

A further preferred solid matrix according to the invention comprises or has a surface comprising a starch-based material. By "starch" according to the invention is preferably understood a combination of two polymeric carbohydrates (polysaccharides), preferably a combination of amylose and amylopectin. Starches according to the invention are insoluble in water. They can be digested by hydrolysis, preferably catalysed by enzymes called amylases, which can break the glycosidic bonds between the "alpha-glucose" components of the starch polysaccharide. The resulting sugars can then be processed, for example, by further enzymes such as maltase.

Another solid matrix preferred according to the invention comprises or has a surface comprising a polyester-based material. The polyester-based material can be solubilised by incubation with esterases or lipases.

A further solid matrix preferred according to the invention comprises or has a surface comprising a material based on a chitin or a chitin derivative. By "chitin" according to the invention is preferably understood a material constructed from units of acetylglucosamine, in particular N-acetyl-D-glucos-2-amine, linked together in -1,4 fashion. Chitin can be digested, for example by enzymatic incubation with lysozyme or chitinase, for example from *Bacillus* sp. PI-7S.

In another preferred aspect of the solid matrix according to the invention, it can comprise or have a surface comprising at least one di-, oligo- or polypeptide material. The peptide-based material can be degraded and solubilised by incubation with a protease, for example Proteinase K. Proteinase K is an endolytic protease that cleaves peptide bonds at the carboxylic sides of aliphatic, aromatic or hydrophobic amino acids. Other proteases, for example collagenases, plasmin, subtilisins may be employed, depending on the basis or surface of the solid matrix.

The solid matrix can also comprise or have a surface comprising at least one pectin or derivative thereof. Pectin is preferably understood as primarily comprising an -(α-(1,4) polygalacturonic acid backbone which can be randomly acetylated and methylated. The pectinbased material can be degraded and solubilised by incubation with pectinase and/or pectolyase. Pectinase catalyses the random hydrolysis of 1-4-α-D-galactosiduronic linkages in pectin and other galacturonans. Pectolyase catalyses the eliminative cleavage of (1,4)-α-D-galacturonan methyl ester to give oligosaccharides with 4-deoxy-6-O-methyl-α-D-galact-4-enuronosyl groups at their non-reducing ends.

A further preferred solid matrix according to the invention comprises or has a surface comprising an agar or agarose or a derivative thereof. Agar-based materials can be solubilised by incubation with agarase (agarose 3-glycanohydrolase).

According to another aspect of the system according to the invention, the material of that the solid matrix comprises at least one material that can be transferred into a dissolved or liquid state by alteration of the pH of its environment, preferably in the presence of at least one chaotropic substance and optionally at least one solution of a high ionic strength. It is preferred that the solid matrix is at least partially soluble at a pH other than 7, preferably at a pH within the range from 1 to 6, preferably within the range from 2 to 6, more preferably within the range from 3 to 6, yet more preferably within the range from 4 to 6, even more preferably within the range from 5 to 6, or at a pH within the range from 8 to 14, preferably within the range from 8 to 13, more preferably within the range from 8 to 12, yet more preferably within the range from 8 to 11, even more preferably within the range from 8 to 10, again more preferably within the range from 8 to 9. The material of the solid matrix which is at least partially transferable into soluble state at a pH other than 7 can thus be at least partially transferable into a liquid or dissolved state through contact with a reagent that induces and/or catalyses the transfer into a liquid or dissolved state of the solid matrix through the pH of the reagent. In a preferred embodiment the solid matrix is insoluble in acidic media and soluble in neutral and/or basic media. In another embodiment, the solid matrix is insoluble in basic media and soluble in neutral and/or acidic media. In a further embodiment the solid matrix is insoluble in neutral or physiological-pH media and soluble at acidic and/or basic pH. Numerous pH-dependent reactions triggered by the presence of acid or base, such as by the concentration of $H_3O+$ or $OH-$ ions, are known to those skilled in the art.

Suitable solid matrices which can be transferred into a dissolved or liquid state in a pH-dependent manner are, for example, metastable materials which are stable or almost stable in a first pH range for at least 30 seconds and which dissolve in a different pH range. Preferred materials of this type according to the invention are polymers such as those already known for the encapsulation and release, preferably delayed release, of pharmaceuticals. Polymers which are suitable as solid matrix according to the present invention are preferably copolymers comprising ethylenically unsaturated monomers such as methacrylic acid, acrylic acid, methyl methacrylate, ethyl acrylate, vinyl acetate, as well as derivatives or salts thereof, as well as copolymers comprising naturally occurring polymers, such as celluloses, or derivatives or salts thereof. Preferred are copolymers comprising two or more of the above monomers, for example copolymers comprising two or more ethylenically unsaturated monomers and/or derivatives or salts thereof, copolymers comprising two or more naturally occurring polymers and/or derivatives or salts thereof, copolymers comprising at least one ethylenically unsaturated monomer and/or at least one derivative or salt thereof with at least one naturally occurring polymer and/or at least one derivative or salt thereof. Particularly preferred are copolymers of methacrylic acid and methyl methacrylate in molar ratio 1:1 or 1:2, as, for example, available under the respective trade names Eudragit® L100 with release pH of 6.0 or Eudragit® S100 with release pH of 7.0 (Röhm GmbH), copolymers of methacrylic acid and ethyl acrylate in molar ratio 1:1, such as, for example, the polymer available under the trade name Eudragit® L100-55 with release pH 5.5 (Röhm GmbH), hydroxypropylmethyl cellulose acetate succinate, such as distributed under the trade name Aqoat® with release pH dependent on the chain size, for example with release pH of 5.0 (HPMCAS-LF), of 5.5 (HPMCAS-MF) or of 7.0 (HPMCAS-HF) (ShinEtsu Synthapharm), cellulose derivatives such as cellulose acetate phthalate, for example cellulose derivatives available under the trade name Aquateric® with release pH within the range from 6.2 to 6.5 (FMC Corp), copolymers of vinyl acetate and methacrylic acid in a ratio 9:1, for example as available under the trade name Kollicoat® VAC with release pH within the range 5.8-6.0 (BASF), or polyvinyl derivatives such as polyvinylacetate phthalate, for example as available under the trade name Sureteric® with release pH within the range 4.5-5.5 (Colorcon Ltd.). The release pH is the pH where the polymer mentioned starts to dissolve. Dissolving at the release pH is not a fast process, so the materials could be used for a swab even if the release pH is below the pH of saliva (pH 6 to pH 8). At pH values below the release pH the polymers are substantially insoluble.

According to a further aspect of the present invention it is also possible for a reaction which affects an at least partial transfer of the solid state of the matrix material into a dissolved or liquid state to be catalyzed by both acid and base. For example, the acid- or base-catalyzed hydrolysis of amides, esters and the like can be employed if the solid matrix comprises amide and/or ester linkages. Furthermore, many polysaccharides such as starch and cellulose are insoluble in water. Both cellulose and starch can, however, be degraded into water-soluble mono- and oligosaccharides by acidic and by basic hydrolysis. Accordingly, a pH shift from neutral pH to acidic or basic pH leads to dissolving of starch or cellulose.

The pH is preferably regulated by use of a suitable buffer system. Suitable buffer systems for the pH ranges desired and which are optionally compatible with a biological sample are known to the person skilled in the art.

The system according to the invention and in particular the unit comprising holding element and solid matrix can be prepared by any method which appears suitable to one skilled in the art. A possible method is to first provide a holding element according to the invention, optionally attached to a closure according to the invention, and subsequently to apply the solid matrix to the holding element. The application of the solid matrix to the holding element can be, for example, in the form of at least one application to a holding element according to the invention of a solution or liquid comprising the solid matrix followed by evaporation of solvent from the solid matrix and/or drying thereof, to obtain a substantially dry and/or solid, preferably solid, solid matrix, whereby the application and/or the drying can optionally be repeated as many times as desired, for example to obtain a given size or form of the solid matrix. If the solid matrix is a meltable solid matrix, the application of the solid matrix to a holding element can be carried out at a temperature at which the solid matrix is liquid, semi-liquid or softened and/or formable, followed by cooling to a temperature at which the meltable solid matrix is solid. It is also possible that the application of the solid matrix to the holding element is carried out with assistance from at least one of a support, a template, a form or a mould, for example to achieve a desired size or form of the solid matrix. It is also conceivable that the solid matrix in solid form is brought into contact with a holding element and bound thereto. In this case, the solid matrix is, for example, first applied, for example in a solution, in liquid or semi-liquid form, or as a softened and/or formable material, to at least one of a support, a template, a form or a mould. The solid matrix is then brought into a substantially dry and/or solid form, preferably a solid form, by a method as described above. The solid matrix and a holding element are then preferably brought into contact with each other, preferably bound together, to form the device according to the invention. A binding together of the solid matrix is preferably a physical binding together, such that no chemical bonds form between the solid matrix and the holding element. It is, however, also conceivable that chemical bonds form between the solid matrix and the holding element, or that an adhesive or other binding aid is used to improve or facilitate binding of the solid matrix to the holding element. In the case that an adhesive or other binding aid is used, an adhesive or other binding aid which does not react with or absorb any part of the biological sample or of the solution or liquid comprising the biological sample is preferably selected. It is also preferred in this case that an adhesive or other binding aid does not react with the reagents for transferring the solid matrix into a liquid or dissolved state, or prevent the transfer of the solid matrix into a liquid or dissolved state.

It is also possible that the system according to the invention further comprises at least one element for at least partially transferring the material of the solid matrix into a liquid or dissolved state without disintegration of the biomulecules in the biological sample.

The at least one further element for at least partially transferring the material of the solid matrix from the solid state into a liquid or dissolved state can comprise, for example, at least one releasing aid which assist or cause the at least partial release of the biological sample by at least partial dissolution or disintegration of the solid matrix, such as those agents listed above which change the pH, the ionic strength or the temperature or which comprise at least one enzyme or combinations of at least two thereof.

It is particularly preferred that the solid matrix can be transferred into a dissolved or liquid state using at least one of the above-described reagents or compositions, or any combination thereof which appears suitable to the person skilled in the art, which preferably allows the release of the biomolecules without its being disintegrated, damaged or degraded or otherwise disadvantageously altered with respect to its further treatment.

It is, of course, possible to combine any of the above ways of at least partially transferring the material of the solid matrix into a liquid or dissolved state. The solid matrix can thus be dissolved, for example, by at least one of contacting it with a solvent in which it dissolves and contacting it with a reagent, enzyme, pH modifier or further element which enhances its dissolution, optionally at elevated or decreased temperature. It is also conceivable that, for example, the solid matrix can be contacted with a solvent in which it does not dissolve and then is at least partially dissolved by further contacting with a reagent, enzyme, pH modifier or further element, optionally at elevated or decreased temperature. It is also possible that the solid matrix is first contacted with a reagent, enzyme, pH modifier or further element and then contacted with a solvent, optionally at elevated or decreased temperature. The reagent, enzyme, pH modifier or further element can be in solid or liquid form. The term "liquid form" is understood to mean at least one solvent, or at least one solution in any conceivable solvent or mixture of solvents which is considered suitable by the person skilled in the art, or reagents or compositions which are liquid at the desired operating temperature, as well as melts.

A further contribution to solving the above objects is also provided by a system for collecting a biological sample comprising
    a container having at least one open end,
    a closure fitting on or in the at least one open end,
    a holding element connected to the closure,
    a solid matrix on which the biological sample is deposited, and
    at least one processing agent,
    wherein the material of the solid matrix is at least partially transferable into a liquid or dissolved state by changing at least one physico-chemical property of the environment of the matrix without disintegration of the biological sample deposited on the matrix, preferably in the presence of at least one chaotropic substance and optionally at least one solution of a high ionic strength.

In respect of the biological sample, container, closure, holding element and solid matrix, the details already given above for the container, closure, holding element and solid matrix also apply here.

The at least one processing agent according to the invention is preferably an agent which helps to process the solid matrix or the biological sample or at least one component of the biological sample, or which helps to maintain the integrity of the biological sample or of at least one component thereof, such as the cell or cells or components thereof, the nucleic acids or the proteins. By "processing of the solid matrix" is preferably understood the transfer of the material of the solid matrix into a liquid or dissolved state. By "processing of the biological sample or of at least one component thereof" is preferably understood the treatment, preparation or preliminary treatment and/or preparation of the biological sample or of a component thereof for, for example, storage, analysis or other handling. The processing agent can be, for example, an agent which relates to the stabilization, handling or processing of the biological sample or which affects a property of the solid matrix or of the liquid or dissolved state of the solid matrix. The at least one processing agent is preferably selected from the group consisting of an ionic strength and/or chaotropic stabilizer, a temperature modifier and an enzyme, stabilising agents for a cell, stabilising agents for a cellular component, stabilising agents for a nucleic acid, stabilising agents for a protein, stabilising agents for a macromolecule, stabilising agents for a tissue, lysing agents, inhibitors which inhibit the decomposition of nucleic acids and/or proteins, inhibitors that can effect inhibition of agents that damage macromolecules and modification agents which act against, or reduce the activity of proteases, RNases, DNases or other enzymes for degradation reactions of the biological sample and/or a component thereof. Other possible processing agents can be protein modification agents, such as at least one acetylating agent, halogenating agent, nucleotide, nucleic acid analogue, amino acid or amino acid analogue, carbodiimide or imide, haloacetate, haloacetamide, acetylsalicylic acid or acid anhydride. Other processing agents are also conceivable, such as ionic or non-ionic detergents, reducing agents, such as 2-mercaptoethanol, dithiothreitol, ascorbic acid, antimicrobials, chelating agents, such as ethylene diamine tetraacetic acid (EDTA) and buffer substances other than those used as processing agents, such as HEPES or MOPS.

A solution to the above mentioned objects is also provided by a method for collection of a biological sample comprising bringing into contact the biological sample with a solid matrix connected a holding element connected to a closure fitting on or in at least one container having at least one open end in which said closure is fitting in or on and at least partially transferring said solid matrix from the solid state into a liquid or dissolved state by changing at least one physico-chemical property of the environment of said matrix without disintegration of the biological sample deposited on said matrix.

The bringing into contact of the biological sample with a solid matrix according to the invention preferably occurs by contacting the solid matrix with a sample of saliva, blood, cerebrospinal fluid, urine, or other body fluid or an isolation of cells such as epithelial cells from a living or a dead organism, especially from a human being or an animal.

The bringing into contact of the biological sample and the solid matrix according to the invention preferably occurs at the same time as or immediately after removal of the sample from its natural environment. The term "immediately after removal" indicates that the biological sample is preferably brought into contact with the device within 2 hours of removal from its natural environment, preferably within 1 hour of its removal, more preferably within 30 minutes of its removal, most preferably within 10 minutes of its removal. If the bringing into contact occurs at the same time as the removal of the sample from its natural environment it is preferred that the sample is removed from its natural environment by being contacted with the solid matrix according to the invention. If the contacting of the biological sample with the solid matrix occurs after the sample is removed from its natural environment, it is preferred that the time that elapses between removal of the sample from its natural environment and bringing into contact of the sample with the solid matrix is less than 10 hours, preferably less than 2 hours, more preferably less than 1 hour, yet more preferably less than 30 minutes, even more preferably less than 10 minutes and most preferably less than 1 minute. However it is explicitly not ruled out that the device according to the invention can also be used for samples that were removed from its natural environment for longer time periods. Samples that can be used according to the invention include, besides others, forensic case work samples.

The bringing into contact can occur by any element which is considered by the skilled person to be suitable for the type of sample. Thus, for example, if the sample is a sample of a bodily fluid such as saliva, urine, sweat, blood, semen or the like, or a sample which can be collected by touching, scraping or rubbing with the device, for example epithelial cells or smears, the bringing into contact can occur simply by using the device to remove the sample directly from its natural environment. For many liquid samples a solid matrix which can absorb the liquid is preferred. For other types of sample, for example, a fine needle aspirate or a tissue sample, for example in the form of a biopsy, or also a blood sample, it might be necessary first to collect the sample using different collection element, such as a needle or a cannula, or by cutting the sample, before bringing the biological sample into contact with the device according to the invention.

It is particularly preferred according to the invention that the biological sample is applied to the solid matrix by means of directly contacting the solid matrix with the biological sample and preferably by collecting the biological sample directly from its source using the solid matrix. The biological sample is preferably not poured onto the solid matrix according to the invention.

It is preferred according to the invention that the biological sample does not dry on the solid matrix.

The at least partial transfer of the material of the solid matrix into a liquid or dissolved state occurs by changing at least one physico-chemical property of the environment of the matrix. The at least partial transfer of the material of the solid matrix into a liquid or dissolved state according to the invention preferably results in at least partial release of the biological sample from the solid matrix.

Further details are provided above.

Changing at least one physico-chemical property triggers at least a partial, preferably to at least 10 wt. %, more preferably in an amount of at least 50 wt. %, even more preferably in an amount of at least 75 wt. % and most preferably a full transfer of the material of the solid matrix into a liquid or dissolved state. Physico-chemical properties which can be changed and which are preferred in this context are those mentioned above in connection with the system according to the invention.

It is preferred that the at least one physico-chemical property which is changed is at least one change of physico-chemical property selected from the group consisting of addition of at least one solvent, increasing temperature, addition of at least one reagent, addition of at least one enzyme and alteration of pH. Thus, for example, addition of at least one solvent preferably causes the solid matrix to at least partially dissolve in the solvent; increasing the temperature preferably causes the solid matrix to at least partially melt; addition of at least one reagent and/or at least one enzyme, and/or alteration of pH preferably causes the solid matrix to at least partially become liquid or to dissolve. The solvents, temperatures, reagents, enzymes and pH values preferred for the invention are those mentioned above in connection with the system according to the invention.

It is particularly preferred according to the inventive method that the at least partial transfer of the solid matrix into a liquid or dissolved state is effected by addition of a least one component selected from enzyme(s), solvent(s), acid(s) or base(s), reagent(s).

Any combination of the above physico-chemical property changes can also be applied according to the invention. Thus, it is conceivable that the release of the biological sample is triggered by changing more than one of the above physico-chemical property substantially at the same time, for example by elevating or decreasing temperature substantially at the same time as increasing or decreasing pH and/or adding at least one solvent, reagent and/or enzyme.

It is also conceivable that the method according to the invention comprises a stabilisation of the biological sample or of at least one component thereof, preferably by addition of a stabilising agent. Stabilising agents and other elements of stabilisation of biological materials are well known to the person skilled in the art. It is also possible that a stabilising agent is capable of effecting or assisting transfer of the solid matrix according to the invention from the solid state into a liquid or dissolved state. Stabilisation of the biological sample or of at least one component thereof preferably occurs as soon as possible during or after collection, preferably before or during but also conceivably after transfer of the solid matrix according to the invention into a liquid or dissolved state.

It is also possible that the method according to the invention further comprises the step of transporting the biological sample material which has been contacted with the solid matrix according to the invention. If the biological sample should be transported after having been brought into contact with the solid matrix according to the invention, it is possible that the solid matrix is at least partially transferred from the solid state into a liquid or dissolved state by changing at least one physico-chemical property during transport. Transport in this context can be transport from the source of the sample to a place where the sample can be analysed and/or stored or otherwise prepared or processed. The transport can thus be, for example, simply transport from a patient to a work station in the same or a nearby room. It could also be transport from the source of the sample to a central analysis and/or storage facility, which might involve a delay and/or journey of several hours or days after collection of the sample, although preferably less than 24 hours.

It is also possible that the method according to the invention further comprises the step of isolation of one or more biological components from the biological sample. Isolation of one or more biological components from the biological sample can occur during or after the transfer of the material of the solid matrix into a liquid or dissolved state, preferably after the transfer of the material of the solid matrix into a liquid or dissolved state. All isolation and purification techniques known to the skilled person also come into consideration according to the invention for the isolation and/or purification of the biological sample. The isolation of nucleic acids, for example, preferably occurs after the transfer of the material of the solid matrix into a liquid or dissolved state, whereby the sample is preferably released from the solid matrix and treated with a lysis reagent, preferably by bead membrane or silica membrane based technologies. These methods are particularly easy to automate, for example in an automated or semi-automated system, preferably a high throughput system.

An at least partial transfer of the solid matrix according to the invention from the solid state into a liquid or dissolved state, and an at least partial release of the biological sample from the solid matrix with which it has been contacted, preferably occurs during at least one of stabilization, transport and storage of the solid matrix carrying the biological sample, or in the course of processing and/or purification of the biological sample collected according to the inventive method, preferably during stabilization or transport, more preferably during transport. This represents a particular advantage of the method according to the invention in terms of efficiency and time-saving.

In any of the above combinations and preferred embodiments it is especially preferred that the solid matrix is at least partially transferred into a liquid or dissolved state in the presence of at least one chaotropic substance and optionally at least one solution of a high ionic strength.

The invention also relates to a kit comprising at least one system according to the invention. The kit according to the invention can be, but need not necessarily be, so devised that it can be portable, for example for use both in and outside medical or veterinary facilities or out of doors, for example in hospitals, in doctor's surgeries, in pharmacies, in workplaces, in the home, in law enforcement, in forensics, in environmental sample collecting, in food sample collecting, in plant sample collecting. The kit can further comprise one or more compositions suitable for stabilising and/or treating a broad range of biological samples and/or for transferring the solid matrix of the device according to the invention from the solid state into a liquid state. It is also possible that the kit comprises a specialized composition for a particular sample or type of sample. A portable kit preferably also comprises a suitable carrier for carrying the kit, as well as optionally one or more portable devices capable of heating or cooling the kit, in particular the kit comprising the sample. The kit according to the invention preferably also comprises instructions for using the kit. It is also possible that the kit comprises further components, such as those which might be necessary to fulfil legal purposes in law enforcement, establishment of genetic relationships or workplace testing. Such components can include tape or other tamper-proof sealing elements and/or legal documents.

It is preferred that the system and/or the kit according to the invention is compatible with an at least partially automated system, which can be an automated system or a semi-automated system or, for example, a high throughput system. The at least partially automated system can relate to at least one of storage, retrieval, processing, purification and analysis of a biological sample.

A particular advantage of the invention is that it enables an efficient, fast and reproducible collection, in particular with low loss of sample, stabilisation, processing and/or analysis of a large number of biological samples.

The embodiments and aspects of the invention can of course be combined with each other in any way which appears suitable to the skilled person to achieve the objects of the invention.

The invention is further illustrated by the following non-limiting figures and examples.

DESCRIPTION OF THE FIGURES

FIG. 1 shows different forms of a rod-like unit comprising a closed holding element and a solid matrix:
a) round head;
b) elongated head;
c) bulb-shaped head;
d) paper;
e) teat-shaped head
f) elongated head with a hollow rod containing a fluid or a solid.
g) with a closed circuit passing through the rod and the solid matrix.

Figure 2:
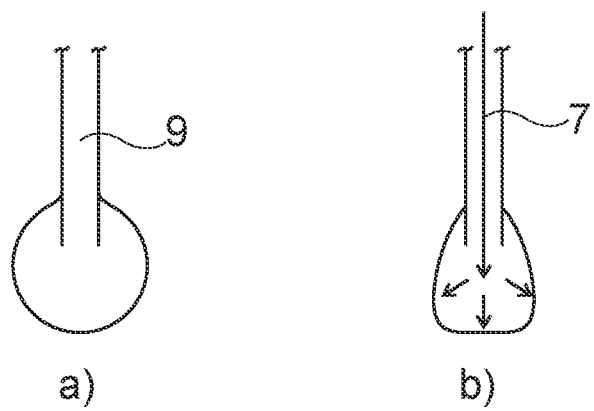
Figure 3:
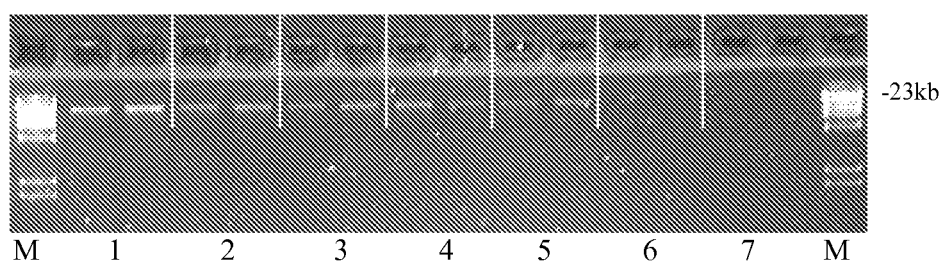

FIG. 2 shows different forms of the rod-like unit comprising a holding element in the form of a hollow rod open to a solid matrix:
a) the basic structure;
b) the basic structure with a fluid flowing through the hollow rod;

FIG. 3 shows an agarose gel electrophoresis with eluates from paraplast swabs melted in reagent A (1), B (2 and 4), C (3 and 5), D (6) and E (7). M: Lambda Hind III molecular weight marker The embodiments of FIG. 1 represent the preferred forms of the system 1 according to the invention. The solid matrix 3 is attached to the holding element 4 in the form of a rod, at the tip 5 of the rod. The rod may be solid or hollow and is, if hollow, closed to the solid matrix 3 of the head.

FIG. 1 f) exemplifies a system with, as holding element, a hollow rod which has a larger opening 6 in the rod at the opposite end to the head, to allow ingress of a fluid 7, for example for cooling or heating, and optionally to act as a reservoir for the fluid 7.

FIG. 1 g) shows an alternative embodiment, whereby a circuit 9 which is closed to the solid matrix 3 is provided by or through the rod, for example for flow of a cooling or heating agent or for passage of a current to warm the solid matrix 3 of the head.

The further aspects depicted in FIG. 2 a) and b) show a hollow rod as holding element which is open to the solid matrix 3 of the head. The cavity 8 provided within the hollow rod can be used to effect or assist a transfer of the solid matrix 3 from the solid state into a liquid or dissolved state, for example by providing a releasing aid.

FIG. 2 b) shows the flow of a fluid 7, for example a cryogen or a releasing aid, through the rod and at least into, preferably through the head.

EXAMPLES

Example 1

Extraction of DNA from a Soluble Buccal Swab Using a Chaotropic Solution

Cellulose acetate fibers in the form of a swab were used for taking buccal swabs from human donors. Swabs were cut into two equally sized pieces (A and B) and DNA was extracted using different procedures.

Procedure 1

Cellulose acetate swab part A was dissolved in 800 µl of Buffer AVL (high salt buffer from QIAGEN containing guanidinium salt) over five minutes at room temperature with gentle agitation. 560 µl of the suspension were transferred into a 2 ml microcentrifuge tube and 560 µl of ethanol added to the tube containing the suspension. Mixing was carried out by vortexing and the sample was transferred onto a column with a membrane (QIAamp Mini Spin column from QIAGEN). The column was centrifuged at 8,000 rpm for one minute to bind nucleic acids to the membrane. The column was washed a first time with 500 µl of AW1 buffer (guanidinium salt and ethanol containing buffer from QIAGEN), followed by centrifugation at 8000 rpm for one minute. The column was then washed a second time with 500 µl of AW2 Buffer (ethanol containing buffer from QIAGEN), followed by centrifugation at 8000 rpm for one minute. In a drying step the column was transferred into a new collection tube and centrifuged for three minutes at 14,000 rpm. For elution, 150 µl of AE buffer (low salt elution buffer from QIAGEN) were dispensed onto the dried membrane followed by centrifugation for one minute at 14,000 rpm.

Genomic DNA in the eluate was quantified using real time PCR. The mean yield for procedure 1 was 8.7 ng of DNA.

Procedure 2

Cellulose acetate swab part B was dissolved in 800 µl aqueous of Buffer AVL (high salt buffer from QIAGEN containing guanidinium salt) over five minutes at room temperature with gentle agitation. 400 µl of the suspension were transferred into a 2 ml microcentrifuge tube. 720 µl of deionized water and 20 µl of proteinase K (from QIAGEN) were added to the tube containing the suspension. Mixing was carried out by vortexing and the sample was incubated at 56° C. for 10 minutes. A further 456 µl of Buffer AVL (from QIAGEN) and 800 µl of ethanol were added and mixing was carried out by vortexing. The sample was then transferred onto a column (QIAamp® Mini Spin column from QIAGEN). The column was centrifuged at 8,000 rpm for one minute to bind nucleic acids to the membrane. The column was washed a first time with 500 µl of Buffer AW1 (from QIAGEN), followed by centrifugation at 8000 rpm for one minute. The column was then washed a second time with 500 µl of Buffer AW2 (from QIAGEN), followed by centrifugation at 8000 rpm for one minute. In a drying step the column was transferred into a new collection tube and centrifuged for three minutes at 14,000 rpm. For elution, 150 µl of Buffer AE (low salt elution buffer from QIAGEN) were dispensed onto the dried membrane followed by centrifugation for one minute at 14,000 rpm.

Genomic DNA in the eluate was quantified using real time PCR. The mean yield for procedure 2 was 50.9 ng of DNA.

Example 2

Solubility of Cellulose Acetate Phthalate in Different Buffers

The solubility of cellulose acetate phthalate (CAP) in different buffers was investigated.

50 mg (+/−1 mg) of CAP were transferred into a 2 ml microcentrifugation tube. 1 ml buffer was added. The tube was closed and subjected to pulse vortexing for 10 seconds to mix the contents. The tube was then observed at room temperature for 30 hours.

The buffers used were ATL (a lysis buffer for bacteria), AVL (a lysis buffer), MTL (a lysis and binding buffer), ML (a lysis and binding buffer), and RLT (a lysis buffer), all of which are commercially available buffers from QIAGEN.

The results are given in the following table 1.

TABLE 1

| Buffer | 30 min | 1 h | 3 h | 10 h | 24 h | 30 h |
|---|---|---|---|---|---|---|
| ATL | CAP beads unaffected | Not swollen, little dissolved | Not swollen, significantly dissolved | Only few small beads visible | CAP beads totally dissolved | CAP beads totally dissolved |
| AVL | CAP beads stick together, swollen | Significantly dissolved | Nearly totally dissolved | CAP beads totally dissolved | CAP beads totally dissolved | CAP beads totally dissolved |
| MTL | CAP beads stick together, swollen | Significantly dissolved | CAP beads totally dissolved | CAP beads totally dissolved | CAP beads totally dissolved | CAP beads totally dissolved |
| ML | CAP beads stick together, swollen | Significantly dissolved | CAP beads totally dissolved | CAP beads totally dissolved | CAP beads totally dissolved | CAP beads totally dissolved |
| RLT | CAP beads stick together, swollen | CAP beads stick together, swollen | Thick, viscous layer on buffer RLT | Thick, viscous layer on buffer RLT | Thick, viscous layer on buffer RLT | Thick, viscous layer on buffer RLT |

Example 3

Extraction of DNA from a Meltable Swab Using a Chaotropic Solution

Swabs with a head made of Paraffin (Paraplast-XTRA, melting point 52° C., McCormick Scientific) were used for taking samples from HeLa cells. Swabs were melted at 70° C. in different solutions with or without chaotropic salts. DNA was extracted using the QIAamp DNA (QIAGEN) procedure.

Procedure

HeLa cells grown as monolayer were washed twice with PBS. Cells samples were taken with swabs with a head made of Paraplast-XTRA shaped as a scraper. The head of the swabs were dissolved in a 2 ml microcentrifuge tube within 500 µl of different reagents with or without a chaotropic salt (Tab. 2, reagent composition). Melting of the swab head was achieved by incubation for 10 min at 72° C. with gentle agitation. After centrifugation at full speed for 1 min (14,000 rpm) the paraplast constituted a solid layer on top of the liquid solution. 400 µl of the liquid solution were retrieved and transferred into a new 2 ml microcentrifuge tube.

After adding 20 μl of proteinase K and incubation for 10 min at 56° C., 200 μl of ethanol (99.5%) was added. Mixing was carried out by vortexing and the sample was transferred onto a column with a membrane (QIAamp Mini Spin column from QIAGEN). The column was centrifuged at 8,000 rpm for one minute to bind nucleic acids to the membrane. The column was washed a first time with 500 μl washing buffer AW1 (QIAamp DNA, QIAGEN), followed by centrifugation at 8000 rpm for one minute. The column was washed a second time with 500 μl washing buffer AW2 (QIAamp DNA, QIAGEN), followed by centrifugation at 8000 rpm for one minute. For a drying step the column was transferred into a new collection tube and centrifuged for one minute at 14,000 rpm. For elution, 100 μl aqueous buffer AE (QIAamp DNA, QIAGEN) were dispensed onto the dried membrane followed by centrifugation for one minute at 10,000 rpm.

The integrity and size of total DNA was analysed by agarose gel electrophoresis. 10 μl of eluate were mixed with 4 μl loading buffer (containing 50% glycerol and bromphenol blue). The samples were applied to a 1% agarose gel in 1×TBE buffer. Electrophoresis was run for 150 min and approximately 2 Volt per cm length of the electrophoresis chamber. DNA was visualised by ethidium bromide staining (Figure Experiment 3).

Performance in PCR was analysed in a quantitative, real-time PCR on an ABI Sequence Detection System ABI PRISM 7700 (Tab. 2, CT values and standard deviations from two independent extractions running in triplicates). 25 μl assay with 2 μl sample as template contained primer and probes for amplification of a 294 bp fragment within exon 3 (forward primer 5'-TCA CCC ACA CTG TGC CCA TCT ACG A-3', reverse primer 5'-CAG CGG AAC CGC TCA TTG CCA ATG G-3', probe 5"-(FAM)ATG CCC TCC CCC ATG CCA TCC TGC GT(BHQ)3') of the human β-actin gene using the QuantiTect Probe PCR kit (QIAGEN).

DNA extracted from swab heads melted within a solution containing chaotropic salt was of high molecular weight with a fragment length of about 23 kb, running as a distinct band on an agarose gel (Figure Experiment 3, rows 1-5). These DNA samples could be amplified by real time PCR leading to CT values in the range between 27 to 29 (Table 2, A to C).

In contrast no DNA band was visible when the swab head was melted in a solution without chaotropic salt and isolated with the method described above (Figure Experiment 3, rows 6 and 7). Consistent with this result CT values in real time PCR were 6 to 7 cycles later in case of reagent solution D or there was no amplification at all in case of reagent solution E (Table 2).

TABLE 2

| Reagent solution | Reagent composition | Beta-Actin qPCR CT-value |
|---|---|---|
| A | Buffer AL (lysis buffer cont. guanidinium salt, QIAamp DNA, QIAGEN), mixed 1:1 with PBS | 27.5 +/− 0.6 |
| B | Buffer AL mixed 3:2 with PBS | 28.6 +/− 0.3 |
| C | Buffer AL mixed 3.5:1.5 with PBS | 28.5 +/− 0.4 |
| D | Phosphate buffered saline (PBS) | 34.4 +/− 1.0 |
| E | Xylol | 40.0 +/− 0.0 |

Figure Experiment 3: see FIG. 3
Agarose gel electrophoresis with eluates from paraplast swabs melted in reagent A (1), B (2 and 4), C (3 and 5), D (6) and E (7). M: Lambda Hind III molecular weight marker.

Example 4

Extraction of Nucleic Acids from a Soluble Swab Using a Chaotropic Solution

Swabs with a head made of cellulose acetate were spiked with saliva and a mixture containing different viral and bacterial pathogens. Swabs were dissolved either in acetone or in a buffer containing chaotropic agents (buffer AVL, QIAGEN). Nucleic acids were extracted using the QIAamp Viral RNA (QIAGEN) procedure.

Procedure

A pathogen mixture containing *Chlamydia trachomatis* and Hepatitis A Virus (HAV) was prepared. 5 ml of saliva was collected in a 50 ml tube. 100 μl aliquots of the saliva and 40 μl aliquots of the pathogen mixture were spiked onto the cellulose acetate swabs. Swabs were transferred into 15 ml tubes containing either 3 ml acetone or 3 ml of AVL Buffer. After inverting 3 times samples were stored for 24 hours at room temperature.

After storage 560 μl of ethanol (99.5%) was added to 700 μl sample. Mixing was carried out by vortexing and 630 μl of the sample was transferred onto a column with a membrane (QIAamp Mini Spin column from QIAGEN). The column was centrifuged at 8,000 rpm for one minute to bind nucleic acids to the membrane. The remaining sample was transferred onto the QIAamp Mini Spin column and the column was centrifuged at 8,000 rpm for one minute. The column was washed a first time with 500 μl washing buffer AW1 (QIAGEN), followed by centrifugation at 8000 rpm for one minute. The column was washed a second time with 500 μl washing buffer AW2 (QIAGEN), followed by centrifugation at 8000 rpm for one minute. For a drying step the column was transferred into a new collection tube and centrifuged for three minutes at 14,000 rpm. For elution, 100 μl aqueous buffer AVE (QIAGEN) was dispensed onto the dried membrane. A 1 Minute incubation was followed by centrifugation for one minute at 10,000 rpm.

The PCR-performance of the extracted nucleic acid was analysed in different real-time PCRs.

*Chlamydia trachomatis*-DNA extracted from dissolved swabs was analysed using the artus *C. trachomatis* TM PCR Kit (QIAGEN) on an ABI Sequence Detection System ABI PRISM 7900 as described by the manufacturer.

HAV-RNA extracted from dissolved swabs was analysed with artus HAV LC RT-PCR Kit (QIAGEN) in a Light Cycler 1.0 from Roche as described by the manufacturer.

All samples dissolved within one hour in acetone as well as AVL. Mean CT values and standard deviations from four samples each extracted in triplicates are shown in table 3.

CT values for *C. trachomatis* target DNA was lower for samples dissolved in Buffer AVL compared to those dissolved in acetone (delta CT=−2.70). CTs for internal controls spiked into the PCR reaction were equal, indicating that inhibition of the PCR is not the reason for the higher target CT values of the acetone samples.

Comparable with the *C. trachomatis* data, in the artus HAV LC RT-PCR the CT values were lower for the samples dissolved in AVL compared to the acetone samples (delta CT=−1.87).

TABLE 3

| | Real-time PCR results | | |
|---|---|---|---|
| Reagent composition | artus C. trachomatis TM PCR Kit target DNA | artus C. trachomatis TM PCR Kit internal control | artus HAV LC RT-PCR Kit target RNA |
| Acetone | 34.4 +/− 1.0 | 25.3 +/− 0.2 | 35.25 +/− 1.0 |
| AVL | 31.7 +/− 0.5 | 25.4 +/− 0.1 | 33.38 +/− 0.3 |

The invention claimed is:

1. A system for collecting a biological sample directly from a source comprising:
   a container having at least one open end,
   a closure fitting on or in said at least one open end,
   a holding element connected to said closure,
   at least one chaotropic substance, and
   a solid matrix on which said biological sample can be deposited, the solid matrix comprising a low melting agarose with a melting point below 65° C.,
   wherein material of said solid matrix is at least partially transferable into a liquid state and/or can be dissolved, in the presence of the at least one chaotropic substance, and optionally in the presence of at least one substance of high ionic strength,
   wherein said matrix is at least substantially solid under collection conditions, and
   wherein said holding element is adapted to hold said solid matrix, and
   further comprising at least one element for at least partially transferring said material of said solid matrix from a solid state into a liquid and/or dissolved state selected from the group consisting of:
      at least one solvent in which the material of said solid matrix is soluble,
      at least one reagent,
      at least one enzyme, and
      at least one pH modifier.

2. The system of claim 1, wherein the system further comprises at least one substance of high ionic strength.

3. A system for collecting a biological sample directly from a source comprising:
   a container having at least one open end,
   a closure fitting on or in said at least one open end,
   a holding element connected to said closure,
   at least one chaotropic substance, and
   a solid matrix on which said biological sample can be deposited, the solid matrix comprising a low melting agarose with a melting point below 65° C.,
   wherein material of said solid matrix is at least partially transferable into a liquid state and/or can be dissolved, in the presence of the at least one chaotropic substance, and optionally in the presence of at least one substance of high ionic strength,
   wherein said matrix is at least substantially solid under collection conditions, and
   wherein said holding element is adapted to hold said solid matrix,
   wherein the system optionally further comprises a device for local heating and/or cooling of the solid matrix; and
   wherein the material of said solid matrix is at least partially meltable by increasing the temperature, and wherein the material of said solid matrix is solid at physiological temperatures and is transferrable to the liquid state at a temperature from 45° C. to 95° C.

4. A system for collecting a biological sample comprising a container having at least one open end,
   a closure fitting on or in said at least one open end,
   a holding element connected to said closure,
   a solid matrix on which said biological sample can be deposited, the solid matrix comprising a low melting agarose with a melting point below 65° C., and
   at least one chaotropic substance,
   wherein material of said solid matrix is at least partially transferable into a liquid and/or dissolved state by changing at least one physico-chemical property of the environment of said matrix without disintegration of biomolecules comprised in said biological sample when said sample is deposited on said matrix, in the presence of the at least one chaotropic substance, and optionally in the presence of at least one substance of high ionic strength,
   wherein said solid matrix is at least substantially solid under collection conditions, and
   wherein said holding element is adapted to hold said solid matrix, and
   further comprising at least one element for changing at least one physico-chemical property of the environment selected from the group consisting of:
      at least one solvent in which the material of said solid matrix is soluble,
      at least one reagent,
      at least one enzyme,
      at least one pH modifier, and
      a device for local heating and/or cooling of the solid matrix.

5. The system of claim 4, further comprising at least one substance of high ionic strength.

6. A kit comprising at least one system according to claim 1.

7. A kit comprising at least one system according to claim 4.

8. A kit comprising at least one system according to claim 2.

9. A kit comprising at least one system according to claim 5.

10. A kit of claim 6 which is compatible with at least one at least partially automated system.

11. A kit of claim 7 which is compatible with at least one at least partially automated system.

12. The system of claim 1, wherein the material of said solid matrix comprises:
   a polymer comprising at least one carboxylic acid-comprising monomer;
   a polymer comprising at least one carboxylic acid group-comprising monomer and at least one ethylenically unsaturated monomer;
   a polymer comprising at least one monomer comprising at least one acid group and at least one ethylenically unsaturated group;
   a polymer comprising at least one monomer comprising at least one ring system, wherein said at least one ring system optionally comprises at least one hetero-atom; or
   a polymer comprising at least one ester group, and
   wherein the element for at least partially transferring said material of said solid matrix from a solid state into a liquid and/or dissolved state comprises a solvent in which the material of said solid matrix is soluble.

13. The system of claim 1, wherein said material of said solid matrix is at least partially transferable into a liquid and/or dissolved state by addition of at least one enzyme, wherein said enzyme is selected from the group consisting of a protease, a cellulase, an amylase, a glycanase, a chitinase, a lysozyme, a lipase, an esterase, a pectinase, a pectolyase, and an agarase, and wherein the element for at least partially transferring said material of said solid matrix from a solid state into a liquid and/or dissolved state comprises said enzyme.

14. The system of claim 1, wherein:
the material of said solid matrix is linked by peptide bonds that are degradable by a protease, and the element for at least partially transferring said material of said solid matrix from a solid state into a liquid and/or dissolved state comprises a protease;
the material of said solid matrix is linked with ester bonds that are degradable by an esterases, and the element for at least partially transferring said material of said solid matrix from a solid state into a liquid and/or dissolved state comprises an esterase; or
the material of said solid matrix is linked by glycosidic bonds that are degradable by polysaccharide-degrading enzymes, and the element for at least partially transferring said material of said solid matrix from a solid state into a liquid and/or dissolved state comprises a polysaccharide-degrading enzyme.

15. The system of claim 4, wherein the change of physico-chemical state comprises addition of at least one solvent in which the material of said solid matrix is soluble, wherein the material of said solid matrix comprises:
a polymer comprising at least one carboxylic acid-comprising monomer;
a polymer comprising at least one carboxylic acid group-comprising monomer and at least one ethylenically unsaturated monomer;
a polymer comprising at least one monomer comprising at least one acid group and at least one ethylenically unsaturated group;
a polymer comprising at least one monomer comprising at least one ring system, wherein said at least one ring system optionally comprises at least one hetero-atom; or
a polymer comprising at least one ester group; and
wherein said at least one element for changing at least one physico-chemical property of the environment comprises the at least one solvent.

16. The system of claim 4, wherein the change of physico-chemical state comprises increasing the temperature, and wherein the material of said solid matrix is solid at physiological temperatures and is transferrable to the liquid state at a temperature from 45° C. to 95° C.

17. The system of claim 4, wherein the change of physico-chemical state comprises addition of an enzyme selected from the group consisting of a protease, a cellulase, an amylase, a glycanase, a chitinase, a lysozyme, a lipase, an esterase, a pectinase, a pectolyase, and an agarase, wherein said material of said solid matrix is hydrolysable by said enzyme, and wherein said at least one element for changing at least one physico-chemical property of the environment comprises said enzyme.

18. The system of claim 4, wherein the change of physico-chemical state comprises addition of an enzyme, and wherein:
the material of said solid matrix is linked by peptide bonds that are degradable by a protease, and the element for changing at least one physico-chemical property of the environment comprises a protease;
the material of said solid matrix is linked with ester bonds that are degradable by an esterases, and the element for changing at least one physico-chemical property of the environment comprises an esterase; or
the material of said solid matrix is linked by glycosidic bonds that are degradable by polysaccharide-degrading enzymes, and the element for changing at least one physico-chemical property of the environment comprises a polysaccharide-degrading enzyme.

19. The system of claim 2, wherein the at least one chaotropic substance and optionally at least one substance of high ionic strength is located within the container.

20. The system of claim 3, wherein the at least one chaotropic substance and optionally at least one substance of high ionic strength is located within the container.

21. The system of claim 3, wherein the system comprises a device for local heating and/or cooling of the solid matrix, wherein said device for local heating and/or cooling of the solid matrix is an opening which extends through the holding element to a region of the holding element adapted to hold the solid matrix, and wherein said opening carries:
an electrical current or a heating substance capable of effecting heating of the solid matrix, or
a cooling substance.

22. The system of claim 4, wherein the at least one chaotropic substance and optionally at least one substance of high ionic strength is located within the container.

23. The system of claim 4, wherein the system comprises a device for local heating and/or cooling of the solid matrix, wherein said device for local heating and/or cooling of the solid matrix is an opening which extends through the holding element to a region of the holding element adapted to hold the solid matrix, without contacting the solid matrix, and wherein said opening carries:
an electrical current or a heating substance capable of effecting heating of the solid matrix, or
a cooling substance.

* * * * *